United States Patent
Brooks

(10) Patent No.: US 10,857,019 B2
(45) Date of Patent: *Dec. 8, 2020

(54) SYSTEM AND METHODS FOR INTERNALIZATION OF EXTERNAL COMPONENTS OF AN ADJUSTABLE INTRAGASTRIC BALLOON

(71) Applicant: SPATZ FGIA, INC., Great Neck, NY (US)

(72) Inventor: Jeffrey Brooks, Ra'anana (IL)

(73) Assignee: SPATZ FGIA, INC., Great Neck, NY (US)

( * ) Notice: Subject to any disclaimer, the term of this patent is extended or adjusted under 35 U.S.C. 154(b) by 232 days.

This patent is subject to a terminal disclaimer.

(21) Appl. No.: 15/949,342

(22) Filed: Apr. 10, 2018

(65) Prior Publication Data

US 2018/0221183 A1 Aug. 9, 2018

Related U.S. Application Data

(63) Continuation of application No. 14/647,372, filed as application No. PCT/US2013/071730 on Nov. 25, 2013, now Pat. No. 9,974,680.

(Continued)

(51) Int. Cl.
*A61F 5/00* (2006.01)

(52) U.S. Cl.
CPC ............ *A61F 5/003* (2013.01); *A61F 5/0036* (2013.01); *A61F 5/0073* (2013.01); *A61F 5/0089* (2013.01)

(58) Field of Classification Search
CPC ...... A61F 5/0036; A61F 5/003; A61F 5/0089; A61F 2002/044; A61F 5/0003;

(Continued)

(56) References Cited

U.S. PATENT DOCUMENTS 3,726,283 A 4/1973 Dye et al.
4,102,342 A 7/1978 Akiyama et al.
(Continued)

FOREIGN PATENT DOCUMENTS

CA 1233387 A1 3/1988
CA 2068715 A1 2/1992
(Continued)

OTHER PUBLICATIONS

Andersen et al, "Randomised trial of endoscopic endoscopic endoprosthesis versus operative bypass in malignant obstructive jaundice", Gut, 30, 1132-1135 (1989).
(Continued)

*Primary Examiner* — Katherine M Shi
(74) *Attorney, Agent, or Firm* — Venable LLP; Michele V. Frank

(57) ABSTRACT

An apparatus for use in a stomach of a subject includes a balloon adapted for placement in the stomach and having an opening to an interior of the balloon, an internal tube in the interior of the balloon with a proximal end coupled to the opening of the balloon, and an inflation tube. The inflation tube has a distal end in the interior of the balloon and a proximal end that can receive a fluid on an exterior of the balloon. The inflation tube can stretch from the stomach to a mouth of the subject to facilitate inflation of the balloon and has a resting position that is substantially within the interior of the balloon. The internal tube is disposed around at least a portion of the inflation tube that is in the interior of the balloon.

20 Claims, 6 Drawing Sheets

Related U.S. Application Data

(60) Provisional application No. 61/770,364, filed on Feb. 28, 2013, provisional application No. 61/729,654, filed on Nov. 26, 2012.

(58) Field of Classification Search
CPC .......... A61M 25/10; A61M 2025/1004; A61M 2025/1068; A61M 2025/1072; A61M 25/1002; A61M 25/1011
See application file for complete search history.

(56) References Cited

U.S. PATENT DOCUMENTS

| | | | |
|---|---|---|---|
| 4,116,201 A | 9/1978 | Shah | |
| 4,129,145 A | 12/1978 | Wynn | |
| 4,311,146 A | 1/1982 | Wonder | |
| 4,315,509 A | 2/1982 | Smit | |
| 4,416,267 A | 11/1983 | Garren et al. | |
| 4,447,227 A | 5/1984 | Kotsanis | |
| 4,485,805 A | 12/1984 | Foster, Jr. | |
| 4,598,699 A | 7/1986 | Garren et al. | |
| 4,694,827 A | 9/1987 | Weiner et al. | |
| 4,696,288 A | 9/1987 | Kuzmak et al. | |
| 4,738,667 A | 4/1988 | Galloway | |
| 4,739,758 A | 4/1988 | Lai et al. | |
| 4,766,628 A | 8/1988 | Walker | |
| 4,813,934 A | 3/1989 | Engelson et al. | |
| 4,878,905 A | 11/1989 | Blass | |
| 4,899,747 A | 2/1990 | Garren et al. | |
| 4,908,011 A | 3/1990 | Jacobsen et al. | |
| 4,925,446 A | 5/1990 | Garay et al. | |
| 5,002,556 A | 3/1991 | Ishida et al. | |
| 5,052,998 A | 10/1991 | Zimmon | |
| 5,084,061 A | 1/1992 | Gau et al. | |
| 5,129,915 A | 7/1992 | Cantenys | |
| 5,167,239 A | 12/1992 | Cohen et al. | |
| 5,234,454 A | 8/1993 | Bangs | |
| 5,259,399 A | 11/1993 | Brown | |
| 5,380,282 A | 1/1995 | Burns | |
| 5,433,216 A | 7/1995 | Sugrue et al. | |
| 5,458,583 A | 10/1995 | McNeely et al. | |
| 5,536,274 A | 7/1996 | Neuss | |
| 5,578,048 A | 11/1996 | Pasqualucci et al. | |
| 5,624,395 A | 4/1997 | Mikhail et al. | |
| 5,724,994 A | 3/1998 | Simon et al. | |
| 5,732,715 A | 3/1998 | Jacobs et al. | |
| 5,827,304 A | 10/1998 | Hart | |
| 5,976,106 A | 11/1999 | Verin et al. | |
| 5,985,307 A | 11/1999 | Hanson et al. | |
| 6,050,972 A | 4/2000 | Zadno-Azizi et al. | |
| 6,127,597 A | 10/2000 | Beyar et al. | |
| 6,183,461 B1 | 2/2001 | Matsuura et al. | |
| 6,213,936 B1 | 4/2001 | Nishioka et al. | |
| 6,245,040 B1 | 6/2001 | Inderbitzen et al. | |
| 6,364,686 B2 | 4/2002 | Gimbel | |
| 6,364,868 B1 | 4/2002 | Ikeguchi | |
| 6,569,173 B1 | 5/2003 | Blatter et al. | |
| 6,616,678 B2 | 9/2003 | Nishtala et al. | |
| 6,652,339 B1 | 11/2003 | Carmichael | |
| 6,656,194 B1 | 12/2003 | Gannoe et al. | |
| 6,712,831 B1 | 3/2004 | Kaplan et al. | |
| 6,743,198 B1 | 6/2004 | Tihon | |
| 6,746,460 B2 | 6/2004 | Gannoe et al. | |
| 7,004,176 B2 | 2/2006 | Lau | |
| 7,033,384 B2 | 4/2006 | Gannoe et al. | |
| 7,056,305 B2 | 6/2006 | Garza Alvarez | |
| 7,087,009 B2 | 8/2006 | Migachyov | |
| 7,147,665 B1 | 12/2006 | Bryan et al. | |
| 7,331,949 B2 | 2/2008 | Marisi | |
| 7,347,868 B2 | 3/2008 | Burnett et al. | |
| 7,470,251 B2 | 12/2008 | Shah | |
| 7,628,821 B2 | 12/2009 | Stack et al. | |
| 7,654,950 B2 | 2/2010 | Yachia et al. | |
| 7,753,928 B2 | 7/2010 | de la Torre et al. | |
| 7,883,524 B2 | 2/2011 | Chen | |
| 8,062,207 B2 | 11/2011 | Gannoe et al. | |
| 8,088,103 B2 | 1/2012 | Teeslink et al. | |
| 8,403,952 B2 | 3/2013 | Brooks et al. | |
| 8,888,739 B2 | 11/2014 | Gregory et al. | |
| 8,939,991 B2 | 1/2015 | Krolik et al. | |
| 9,044,571 B2 | 6/2015 | Pinchuk et al. | |
| 9,308,361 B2 | 4/2016 | Muni | |
| 9,399,121 B2 | 7/2016 | Goldfarb et al. | |
| 9,504,811 B2 | 11/2016 | Tilson et al. | |
| 2001/0020150 A1 | 9/2001 | Ravo | |
| 2002/0045914 A1 | 4/2002 | Roberts et al. | |
| 2002/0055757 A1 | 5/2002 | Torre et al. | |
| 2002/0151923 A1 | 10/2002 | Holzer | |
| 2003/0158569 A1 | 8/2003 | Wazne | |
| 2003/0171768 A1 | 9/2003 | McGhan | |
| 2003/0191492 A1 | 10/2003 | Gellman et al. | |
| 2004/0030347 A1 | 2/2004 | Gannoe et al. | |
| 2004/0044357 A1 | 3/2004 | Gannoe et al. | |
| 2004/0059289 A1 | 3/2004 | Garza Alvarez | |
| 2004/0064893 A1 | 4/2004 | Sharp | |
| 2004/0088008 A1 | 5/2004 | Gannoe et al. | |
| 2004/0093091 A1 | 5/2004 | Gannoe et al. | |
| 2004/0167625 A1 | 8/2004 | Beyar et al. | |
| 2004/0193092 A1 | 9/2004 | Deal | |
| 2004/0225247 A1 | 11/2004 | Pugsley et al. | |
| 2004/0267378 A1 | 12/2004 | Gazi et al. | |
| 2005/0004430 A1 | 1/2005 | Lee et al. | |
| 2005/0033331 A1 | 2/2005 | Burnett et al. | |
| 2005/0033345 A1 | 2/2005 | DeLegge | |
| 2005/0055039 A1 | 3/2005 | Burnett et al. | |
| 2005/0070937 A1 | 3/2005 | Jambor et al. | |
| 2005/0085923 A1 | 4/2005 | Levine et al. | |
| 2005/0096750 A1 | 5/2005 | Kagan et al. | |
| 2005/0125020 A1 | 6/2005 | Meade et al. | |
| 2005/0192614 A1 | 9/2005 | Binmoeller | |
| 2005/0192629 A1 | 9/2005 | Saadat et al. | |
| 2005/0209674 A1 | 9/2005 | Kutscher et al. | |
| 2005/0216040 A1 | 9/2005 | Gertner et al. | |
| 2005/0228504 A1 | 10/2005 | Demarais | |
| 2005/0256460 A1 | 11/2005 | Rome et al. | |
| 2005/0267361 A1 | 12/2005 | Younker et al. | |
| 2005/0267595 A1 | 12/2005 | Chen et al. | |
| 2005/0267596 A1 | 12/2005 | Chen et al. | |
| 2006/0020278 A1 | 1/2006 | Burnett et al. | |
| 2006/0058892 A1 | 3/2006 | Lesh et al. | |
| 2006/0100479 A1 | 5/2006 | Yachia et al. | |
| 2006/0142731 A1 | 6/2006 | Brooks | |
| 2006/0190019 A1 | 8/2006 | Gannoe et al. | |
| 2006/0206064 A1 | 9/2006 | Kagan et al. | |
| 2006/0271088 A1 | 11/2006 | Alfrhan | |
| 2007/0083224 A1 | 4/2007 | Hively | |
| 2007/0088380 A1 | 4/2007 | Hirszowicz et al. | |
| 2007/0118168 A1 | 5/2007 | Lointier et al. | |
| 2007/0149994 A1 | 6/2007 | Sosnowski et al. | |
| 2007/0173881 A1 | 7/2007 | Birk et al. | |
| 2007/0239284 A1 | 10/2007 | Skerven et al. | |
| 2008/0147012 A1 | 6/2008 | Rome | |
| 2008/0172079 A1 | 7/2008 | Birk | |
| 2008/0208135 A1 | 8/2008 | Annunziata | |
| 2009/0152379 A1 | 6/2009 | Harter | |
| 2009/0164028 A1 | 6/2009 | Chen | |
| 2009/0171382 A1 | 7/2009 | Dillon et al. | |
| 2009/0287231 A1 | 11/2009 | Brooks et al. | |
| 2010/0121371 A1* | 5/2010 | Brooks | A61F 5/003 606/192 |
| 2010/0252464 A1 | 10/2010 | Belitz | |
| 2010/0274189 A1 | 10/2010 | Kurth et al. | |
| 2011/0092998 A1 | 4/2011 | Hirszowicz et al. | |
| 2011/0218563 A1 | 9/2011 | Brooks et al. | |
| 2012/0191123 A1 | 7/2012 | Brister et al. | |
| 2012/0296365 A1 | 11/2012 | Nguyen | |
| 2013/0035710 A1 | 2/2013 | Bouasaysy et al. | |
| 2013/0255807 A1 | 10/2013 | Bonzon et al. | |
| 2014/0249374 A1 | 9/2014 | Evans et al. | |
| 2016/0100946 A1 | 4/2016 | Fogarty et al. | |
| 2016/0193064 A1 | 7/2016 | Brister et al. | |
| 2016/0310306 A1 | 10/2016 | Brister et al. | |
| 2017/0007310 A1 | 1/2017 | Rajagopalan et al. | |
| 2017/0156909 A1 | 6/2017 | Brister et al. | |

(56) References Cited

U.S. PATENT DOCUMENTS

| | | | |
|---|---|---|---|
| 2017/0325982 A1 | 11/2017 | Brooks et al. |
| 2017/0354437 A1 | 12/2017 | Bacich |
| 2018/0209553 A1 | 7/2018 | Weaver |
| 2018/0221184 A1 | 8/2018 | Brooks et al. |

FOREIGN PATENT DOCUMENTS

| | | | |
|---|---|---|---|
| CA | 2483335 A1 | 3/2005 |
| DE | 3227585 A1 | 5/1983 |
| DE | 3326061 A1 | 2/1984 |
| DE | 3310234 A1 | 9/1984 |
| DE | 3540936 C1 | 10/1986 |
| EP | 246999 A1 | 11/1987 |
| EP | 1342458 B1 | 8/2005 |
| EP | 2004269 B1 | 8/2016 |
| GB | 2090747 A | 7/1982 |
| GB | 2139902 A | 11/1984 |
| IT | 1235492 B | 9/1992 |
| JP | 2008517677 A | 5/2008 |
| WO | 1986006611 A1 | 11/1986 |
| WO | 1987000034 A2 | 1/1987 |
| WO | 1998056321 A1 | 12/1998 |
| WO | 2001066166 A2 | 9/2001 |
| WO | 2002040081 A2 | 5/2002 |
| WO | 2003055420 A1 | 7/2003 |
| WO | 2003095015 A1 | 11/2003 |
| WO | 2004014237 A1 | 2/2004 |
| WO | 2004089262 A2 | 10/2004 |
| WO | 2004105622 A1 | 12/2004 |
| WO | 2005009288 A2 | 2/2005 |
| WO | 2005039457 A1 | 5/2005 |
| WO | 2005094257 A2 | 10/2005 |
| WO | 2005107641 A2 | 11/2005 |
| WO | 2005094257 A3 | 1/2006 |
| WO | 2006047708 A2 | 5/2006 |
| WO | 2007110866 A3 | 10/2007 |
| WO | 2008132745 A2 | 11/2008 |
| WO | 2006070361 A3 | 4/2009 |
| WO | 2011041864 A1 | 4/2011 |
| WO | 2016/200612 A1 | 12/2016 |
| WO | 2018146547 A1 | 8/2018 |

OTHER PUBLICATIONS

Borowski A et al., "Minimally Invasive, Nonendoscopic Saphenectomy for Coronary Bypass Surgery", J Card Surg 16(6): 484-6, (2001)—an abstract.
Cope, "Improved Anchoring of Nephrostomy Catheters: Loop Technique", American J of Roetngenology 1980.
Dondelinger et al, "Percutaneous management of intraperitoneal, hepatic and other fluid collections", Baillieres Clin Gastroenterol (1992).
Dumon, J.R. et al., "A new method of esophageal dilation using Savary-Gilliard Bougies," Gastro Endosc 31:379-82, 1985.
Fleischer, D.E. et al., "A marked guidewire facilitates esophageal dilation," Am J Gastro 84:359-61, 1989.
Gronval et al , "Ultrasound-guided Drainage of Fluid-containing Masses Using Angiographic Catheterization Techniques", Am J Roetgenol (1977).
Kadakia, SC et al., "Esophageal dilation with polyvinyl bougies using a marked guidewire without the aid of fluoroscopy," Am J Gastro 88:1381-86, 1993.
Lambiase, "Percutaneous Abscess and Fluid Drainage: A Critical Review", Cardiovascular and interventional radiology 14: 143-157 (1991).

Parker et al. "Esophageal dilation with polyvinyl bougies, using a marked guidewire without the aid of fluoroscopy: an update", Am J Gastroenterol. (Sep. 1993); 88(9):1381-6—an abstract.
Shepherd et al, "Endoscopic biliary endoprosthesis in the palliation of malignant obstruction of the distal common bile duct: a randomized trial", British journal of surgery, vol. 75, pp. 1166-1168 (1988).
Speer et al, "Randomised Trial of Endoscopic Versus Percutaneous Stent Insertion in Malignant Obstructive Jaundice", The Lancet (1987).
Van sonnenberg et al, "Percutaneous Abscess Drainage: Current Concepts", Radiology (1991).
Werth, et al., "A safe and quick method for endoscopic retrieval of multiple gastric foreign bodies using a protective sheath," Surg Gynecol Obstet 171(5):419-20, 1990.
CN200580048692.6: English Translation of an Office Action dated Apr. 13, 2010.
EP07736138: European Search Report (Supplementary) dated Jul. 26, 2013.
EP11161677.7: European Search Report dated Aug. 22, 2011.
IL183649: Office Action dated Jan. 21, 2010, and English translation.
JP548959/2007: Office Action dated Apr. 26, 2011, and English translation.
JP2009-502330: Office Action dated Feb. 17, 2012.
JP2011-056619: Office Action dated Oct. 16, 2012.
PCT/IL05/01381: International Search Report dated May 28, 2008.
PCT/IL07/00398: International Search Report dated Sep. 22, 2008.
PCT/IL08/00579: International Search Report dated Dec. 23, 2008.
PCT/IL10/00833: International Search Report dated Feb. 10, 2011.
PCT/US2013/071730: International Search Report and Written Opinion dated Mar. 10, 2014.
U.S. Appl. No. 11/132,855: Office Action dated Oct. 16, 2008.
U.S. Appl. No. 11/132,855: Office Action dated Jun. 11, 2009.
U.S. Appl. No. 11/132,855: Office Action dated Dec. 30, 2009.
U.S. Appl. No. 11/132,855: Office Action dated Jun. 25, 2010.
U.S. Appl. No. 11/132,855: Office Action dated Aug. 24, 2011.
U.S. Appl. No. 11/132,855: Office Action dated Mar. 27, 2012.
U.S. Appl. No. 11/718,795,: Office Action dated Sep. 17, 2010.
U.S. Appl. No. 11/721,993: Office Action dated Feb. 27, 2012.
U.S. Appl. No. 12/598,110: Office Action dated Dec. 13, 2011.
U.S. Appl. No. 12/903,448: Office Action dated Sep. 18, 2012.
U.S. Appl. No. 60/639,843.
U.S. Appl. No. 60/787,124.
U.S. Appl. No. 60/815,624.
Indian Examination Report issued in corresponding Indian Application No. 9024/DELNP/2008 dated Jan. 27, 2017 (9 pages).
U.S. Appl. No. 62/457,056.
International Search Report and Written Opinion issued in related International Application No. PCT/IB18/00173 dated Jul. 12, 2018.
Office Action issued in U.S. Appl. No. 12/598,110 dated Nov. 7, 2013 [Available in IFW].
International Search Report and Written Opinion issued in related International Patent Application No. PCT/US2019/067921 dated Mar. 10, 2020.
Office Action issued in U.S. Appl. No. 15/893,387 dated Feb. 5, 2020 [Available in IFW].
Office Action issued in U.S. Appl. No. 11/718,795 dated Jul. 8, 2011 [Available in IFW].
Office Action issued in U.S. Appl. No. 11/718,795 dated Oct. 9, 2012 [Available in IFW].
Office Action issued in U.S. Appl. No. 14/647,372 dated Oct. 2, 2017 [Available in IFW].
Office Action issued in related Indian Patent Application No. 9024/DELNP/2008 dated Nov. 5, 2019.
Office Action issued in U.S. Appl. No. 15/893,387 dated May 12, 2020 [Available in IFW].

\* cited by examiner

SYSTEM AND METHODS FOR INTERNALIZATION OF EXTERNAL COMPONENTS OF AN ADJUSTABLE INTRAGASTRIC BALLOON

CROSS-REFERENCE TO RELATED APPLICATIONS

This application is a Continuation of U.S. patent application Ser. No. 14/647,372, filed May 26, 2015, which is a U.S. National Stage Application of PCT/US2013/071730, filed Nov. 25, 2013, which claims priority to U.S. Provisional Application No. 61/729,654, filed Nov. 26, 2012, and to U.S. Provisional Application No. 61/770,364, filed Feb. 28, 2013, each of which is incorporated by reference in its entirety.

This application cross-references the following U.S. Patent Applications No. 11/132,855, filed May 18, 2005 and published as U.S. Patent Application Publication No. 2006/0142731 on Jun. 29, 2006; Ser. No. 11/721,993, filed Feb. 26, 2009 as a continuation of U.S. patent application Ser. No. 11/132,855 and patented as U.S. Pat. No. 8,403,952 on Jan. 21, 2010; Ser. No. 11/718,795, filed Jul. 9, 2007 and patented as U.S. Pat. No. 8,430,894 on Apr. 30, 2013; and Ser. No. 13/108,487, filed May 16, 2011 and patented as U.S. Pat. No. 8,430,895 on Apr. 30, 2013, the disclosures of which are incorporated herein by reference in their entireties.

TECHNICAL FIELD OF THE INVENTION

The present invention relates generally to systems and methods directed to adjustable intragastric balloons, and more particularly, to systems and methods for internalizing components of an adjustable intragastric balloon.

BACKGROUND OF THE INVENTION

Morbid obesity remains an ever-growing problem in the world. Varying forms of gastric bypass surgery have developed and have improved over the last few decades. Recently, laparoscopic gastric banding has emerged as a less invasive surgical option. However, bariatric surgery is fraught with morbidity of up to 20%, with a re-operation rate approaching 25% at 3-5 years post-op. Bariatric surgery carries an operative mortality of 0.5%. Diet and pharmaceutical alternatives have not been very effective, with a high recidivism rate. Intragastric balloons in use can achieve weight loss and a drop in BMI. However, balloon deflation can result in unwarranted migration leading to obstruction.

U.S. Pat. Nos. 8,430,894 and 8,430,895 describe balloon systems having a balloon coupled to a gastrointestinal anchor that is configurable to prevent passing of the anchor into a duodenum of a subject. These balloon systems also each describe a stretchable inflation tube that can stretch from a stomach to a mouth of the subject, about 2.5-10 times its length, to facilitate inflation or adjustment of volume of the balloon. The inflation tube is partly inside and partly outside of the balloon. U.S. Patent Application Publication No. 2006/0142731 and U.S. Pat. No. 8,403,952 describe a floating anchor that can be used, for example, with a gastrointestinal balloon. However, further improvements can be made to limit side effects from implantable devices including, but not limited to, tissue trauma, difficulty finding the tube, and difficulty grasping the tube, some of which may result of components of the devices that are located on the outside of the gastrointestinal balloon.

Intragastric balloons still need to be improved upon with respect to adaptation to the body, monitoring, adjustment, and removal.

BRIEF SUMMARY OF THE INVENTION

Embodiments of the invention may provide an apparatus for use in a stomach of a subject. The apparatus comprises a balloon adapted for placement in the stomach and having an opening to an interior of the balloon, an internal tube in the interior of the balloon with a proximal end coupled to the opening of the balloon, and an inflation tube having a distal end in the interior of the balloon and a proximal end configured to receive a fluid on an exterior of the balloon, the inflation tube being configured to stretch from the stomach to a mouth of the subject to facilitate inflation of the balloon and to have a resting position that is substantially within the interior of the balloon, the internal tube being disposed around at least a portion of the inflation tube that is in the interior of the balloon.

Embodiments of the invention may also include a method of adjusting an inflation level of a balloon inserted into a stomach of a subject where the balloon is in fluid communication with an inflation tube. The method comprises stretching the inflation tube while keeping the balloon in the stomach, the inflation tube extending from within the balloon when stretching, transferring a fluid to or from the balloon via the inflation tube which may or may not require connection to an extension tube, to adjust the inflation level of the balloon, and returning the inflation tube to a resting position after adjusting the inflation level, a substantial portion of the inflation tube being contained within the balloon in the resting position.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION

Figure 1A:
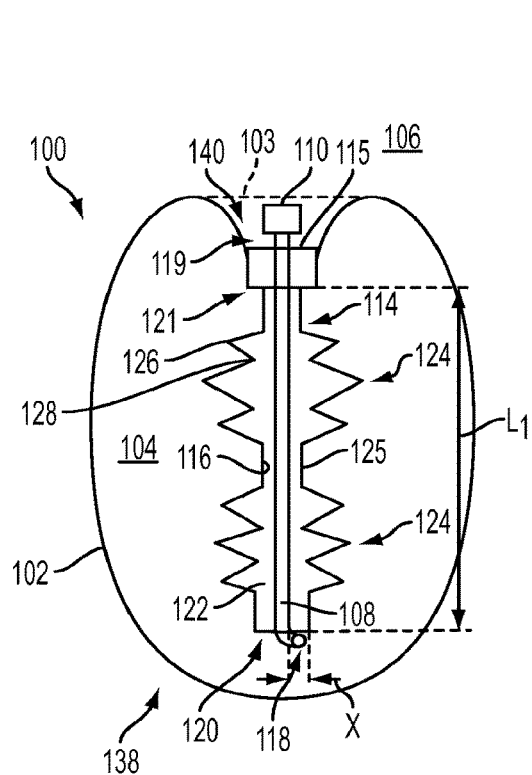
FIG. 1A shows an intragastric balloon with an internal tube in an extended position and an inflation tube disposed substantially inside the balloon in accordance with an embodiment of the invention.

An adjustable balloon may be a fluid filled balloon that has a stretchable inflation tube connected to the balloon. The inflation tube exits the balloon within a surrounding tube and ends in a valve. During an insertion procedure, a pusher and a firm guidewire within the pusher may connect to the balloon and an external catheter in one straight continuum. Alternatively, the balloon may be carried by the endoscope into the stomach using a sleeve connected to the endoscope, and without need of a guidewire. The inflation tube may stretch about 6 to 10 times its length, and may allow the valve to be pulled out of the stomach while the balloon remains in the stomach. This can allow adjustment of the volume of the balloon. Applicant's other patent applications referenced and incorporated above discuss some features of a similar balloon.

An adjustable balloon system may have a stretchable inflation tube that is partly within and partly outside of the balloon. An external tube can produce challenges in several ways, including but not limited to causing tissue trauma, difficulty in finding the tube, and difficulty in grasping the tube.

Embodiments described herein provide systems and methods to internalize the external components into the balloon. In an embodiment, an internal rigid catheter may house a stretchable inflation tube that can be bonded in its most distal 1 cm to an internal surface of the rigid catheter, thereby allowing a remainder of the length of the stretchable inflation tube to slide freely within a lumen of the rigid catheter and thereby attaining its maximum stretchability outside of the balloon. For example, a 10 cm long inflation tube bonded in this way in its most distal 1 cm has a remaining 9 cm of length that is unbound and may stretch to lengths of 60-90 cm. The rigid catheter inside the balloon may be one stagnant length and may only hold a set length of stretchable inflation tube. In some embodiments, the internal rigid catheter can be made to have changeable lengths such that at a resting state it is one length, but when pulled by the bonded end of the inflation tube it can shorten partially and thereby send more stretchable inflation tube to the exterior of the balloon. This in turn can shorten the necessary length of the external inflation tube.

In an embodiment, the internal rigid catheter may have have segments of accordion-like walls that may contract when pulled to shorten the length of the rigid catheter. The thickness of the accordion walls can be varied so that they can have more or less propensity to return to a baseline longer length. Additionally, a metal spring can be provided (internal to or immediately surrounding the catheter) that promotes lengthening of the rigid catheter. Alternatively, a distal end of the variable sized catheter can be bound to a distal end of a surrounding fixed length catheter by a stretchable tether or spring that promotes lengthening of the catheter to its longer length. Alternatively, the distal end of the variable sized catheter can be bound to a distal balloon wall by a stretchable tether or spring that promotes lengthening of the catheter to its longer length.

In an embodiment, the variable sized catheter can be formed as an antenna-type tube, similar to an old-fashioned television antenna, that houses progressively smaller diameter tubes so that the variable sized catheter can shorten or lengthen as desired. The inflation tube can sit inside the smallest diameter segment. The smallest diameter segment would therefore be large enough to house the inflation tube and may have a clearance, for example, at least 1 mm of space, between the inflation tube and catheter wall. Additionally, a metal spring can be provided (internal to or immediately surrounding the catheter) to promote lengthening of the variable sized catheter. The variable sized catheter can also be can be bound to the distal end of a surrounding fixed length catheter by a stretchable tether or spring that promotes lengthening of the collapsible catheter to its longer length. Alternatively, the variable sized catheter can be bound to the distal balloon wall by a stretchable tether or spring that promotes lengthening of the catheter to its longer length.

In some embodiments, systems and methods are provided for internalizing within the balloon an external catheter, valve and cap. The result may provide a smooth balloon without substantial external protrusions. This result can be accomplished according to various embodiments discussed herein. In an embodiment, the area of the balloon from which exits the catheter will be shaped to form a concavity or recess, that is deep enough to hold the valve and cap, For example, the concavity may be approximately 1-5 cm deep. The concavity may be created by differing the density of a material such as silicone or adding other materials to the wall of the balloon in the area of the concavity. Alternatively, the balloon can be lengthened such that the internal catheter can be longer and house more inflation tube so that less protrudes outside of the balloon. The longer balloon can be spherical, pear shaped, cylindrical, or have other shapes that fit in the stomach. The inflation tube may stretch about 6-10 times its length. Alternatively, the inflation tube may be constructed of different materials, such as a different silicone material, and may be able to stretch 10-20 times its length. Alternatively, the internal catheter that houses the inflation tube, and may be a solid straight silicone catheter in an embodiment, can be modified to house a substantially frictionless internal canal that houses the inflation tube. For example, the substantially frictionless internal canal may be lined with Teflon® or other similar materials, or may be filled with liquid silicone oil or other friction reducing material. Reducing the friction in these or other ways would allow the catheter to have a curved shape, such as a shape in a sinusoidal pattern, effectively lengthening the catheter and enabling more inflation tube to be inside the balloon. The catheter may be one piece that starts internally and is glued to the top of the balloon after which it exits the balloon. Alternatively, the catheter may be completely internal catheter that ends in a receptacle at its glue point with the balloon. The receptacle may be big enough to house all or substantially all of the valve and cap. Any combination of the above can accomplish the internalization of the external catheter, valve and cap. Additionally, a supporting frame that can also act as an anchor may also be provided in combination with any of the above features.

Figure 1B:
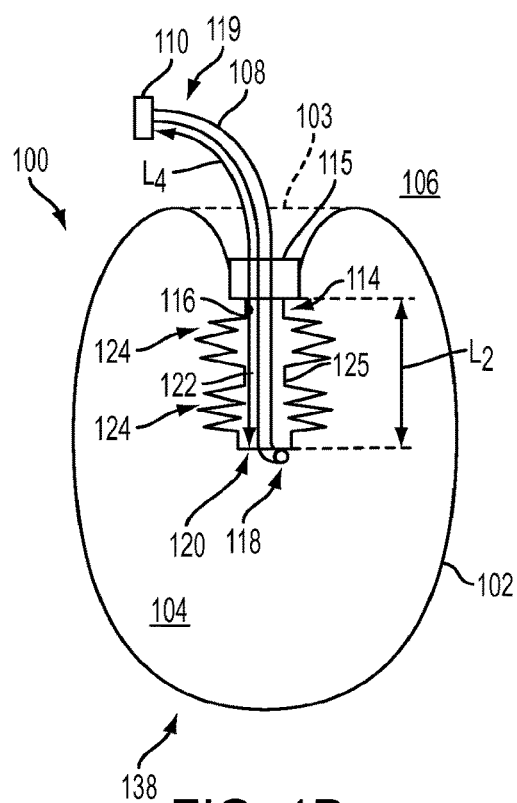
FIG. 1B shows the intragastric balloon of FIG. 1A with the internal tube in a shortened position and the inflation tube disposed with a substantial portion outside the balloon in accordance with an embodiment of the invention.

FIGS. 1A and 1B show an intragastric balloon assembly 100 according to an embodiment of the invention. The assembly 100 generally includes balloon 102 with a substantial internally disposed inflation assembly that can maintain the balloon 102 profile when the inflation assembly is dormant (FIG. 1A), but can be adapted for operational use outside the balloon 102 profile, as shown in FIG. 1B. This can be accomplished through the use of an internal tube 114 alone or in combination with a recess 140. The assembly 100 includes a balloon 102 adapted for placement in the stomach of a subject. The balloon 102 has an opening 115 to an interior 104 of the balloon 102. An inflation tube 108 has a distal end 118 and a proximal end 119. The distal end 118 is positioned in the interior 104 of the balloon 102. The proximal end 119 is adapted to receive a fluid and may be positionable on an exterior 106 of the balloon 102. An internal tube 114 in the interior 104 has a proximal end 121 coupled to the opening 115 of the balloon 102. The inflation tube 108 is contained within a lumen 122 defined by an inner wall 116 of the internal tube 114. A distal end 120 of the internal tube 114 is coupled to the distal end 118 of the inflation tube 108.

The inflation tube 108 can stretch from the stomach to a mouth of the subject to facilitate inflation of the balloon 102. However, in a resting position as shown in FIG. 1A, the inflation tube 108 is substantially within the balloon 102. It can be in the interior 104 of the balloon 102, substantially within the interior 104 of the balloon, or within the general profile of the balloon, which is shown in FIG. 1A by a representative broken line 103. In some embodiments, the recess 140 may have a depth ranging from 10 to 50 mm. The resting position corresponds to a position before the inflation tube 108 is stretched away from the balloon or after the inflation tube 108 has been released from the stretched position and returned to the resting position. According to this internalization of components in the resting position, it may be possible to limit or avoid trauma to tissue of the patient that may otherwise be caused by portions of an intragastric balloon assembly, such as a inflation tube, cap and valve, or other catheter, that protrude from the balloon or profile of the balloon. The returning to the resting position after being stretched may be facilitated by the shrinking or un-stretching of the inflation tube 108, or by the elongation of the internal tube 114 which pulls the distal end 118 of the inflation tube 108, or by a combination of both mechanisms. The internal tube 114 is positioned around at least a portion of the inflation tube 108 that is in the interior 104 of the balloon 102. In some embodiments, a distance x separates the inflation tube 108 from the interior wall 166 of the internal tube 114 to facilitate the stretching and/or sliding of the inflation tube 108 relative to the interior wall 166.

As shown in FIGS. 1A and 1B, the internal tube 114 may have a variable length including a first length $L_1$ that accommodates a substantial portion of the inflation tube 108 when the inflation tube 108 is in the resting position (see FIG. 1A), and a second length $L_2$, which is shorter than the first length $L_1$, when the inflation tube 108 is stretched outwardly from the balloon 102 (see FIG. 1B). The inflation tube 108 has an un-stretched length $L_3$ in the resting position and a stretched length $L_4$ in the stretched position.

The wall of the internal tube 114 in FIG. 1 has a plurality of accordion structures 124 to facilitate the variable length of the internal tube 114. In the example shown in FIGS. 1A and 1B, each of the two accordion structures 124 includes three peaks 126 and two valleys 128 between the peaks 126. However, the internal tube 114 is not limited to this configuration and may have one or more accordion structures 124 that each has at least one, but possibly more, peak 126 and/or valley 128. Multiple accordion structures 124 may be separated by flat portions 125 of the internal tube 114. As shown in FIG. 1B, the accordion structures 124 contract or collapse to allow shortening of the internal tube 114 away from a distal end 138 of the balloon when the inflation tube 108 is stretch outwardly from the balloon 102. Further, upon release of the stretched inflation tube 108 shown in FIG. 1B, the inflation tube 108 and internal tube 114 may return to the resting position show in FIG. 1A. By returning to this resting position, components of the balloon assembly 100 may be contained within or substantially within the balloon or the balloon profile. Thus, trauma to tissues of the patient may be limited or prevented that may have otherwise been caused from protruding portions or an irregular profile of an intragastric balloon according to other constructions.

The opening 115 of the balloon 102 may be formed as a cylindrical structure that is recessed with respect to the walls of the balloon 102 on either side of the opening 115. In addition, the opening 115 may be sized to accommodate one or more structures, such as a cap and valve 110, on the proximal end 119 of the inflation tube 108.

Figure 2A:
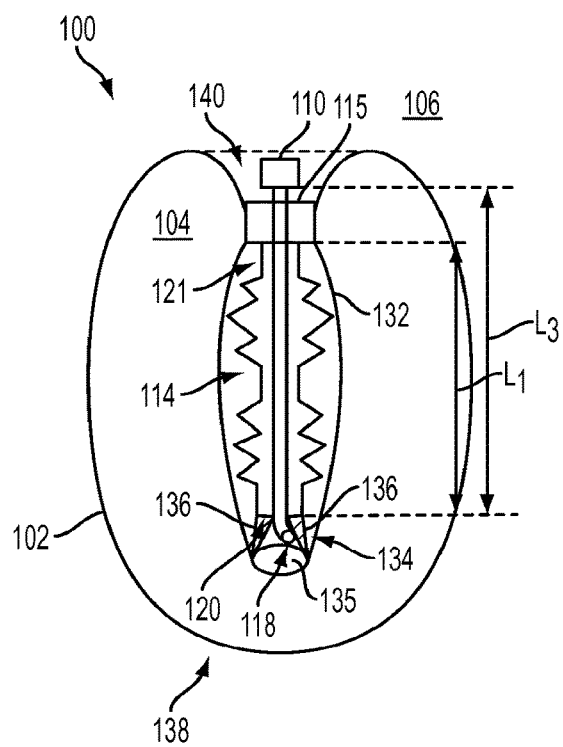
FIG. 2A shows an intragastric balloon with an internal tube in an extended position within a rigid support and a tether at a resting length, and an inflation tube disposed substantially inside the balloon in accordance with an embodiment of the invention.
Figure 2B:
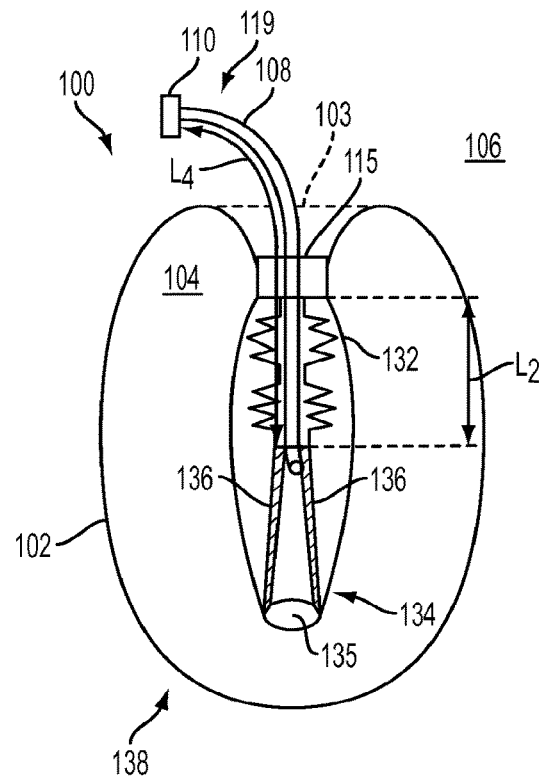
FIG. 2B shows the intragastric balloon of FIG. 2A with the internal tube in a shortened position within the rigid support and tether at a stretched length, and the inflation tube disposed with a substantial portion outside the balloon in accordance with an embodiment of the invention.

FIGS. 2A and 2B show an intragastric balloon assembly 100 according to an embodiment of the invention that includes a rigid support structure 132. The rigid support structure 132 remains fixed as the internal tube 114 varies in length. A distal end 134 of the rigid support structure 132 may be coupled to the distal end 120 of the internal tube 114 via one or more stretchable tethers or springs 136. The tether or spring 136 biases the internal tube 114 to its lengthened position so that the inflation tube 108 and any other external structures will be pulled in or toward the interior 104 of the balloon 102. In some embodiments, a tether or spring may be coupled to the distal wall 138 of the balloon 102, rather than the rigid support structure 132.

The rigid support structure 132 may define an opening 135 at its distal end 134 allow fluid to flow to and from the inflation tube 108 to the remainder of the balloon 102. The rigid support structure 132 may be substantially coaxial with the internal tube 114.

Figure 3A:
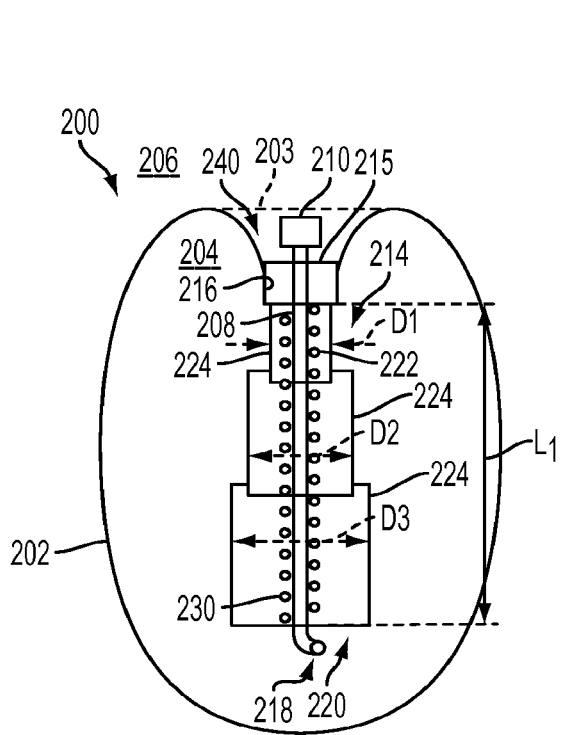
FIG. 3A shows an intragastric balloon with a telescoping internal tube in an extended position with the spring at the resting length and an inflation tube disposed substantially inside the balloon in accordance with an embodiment of the invention.
Figure 3B:
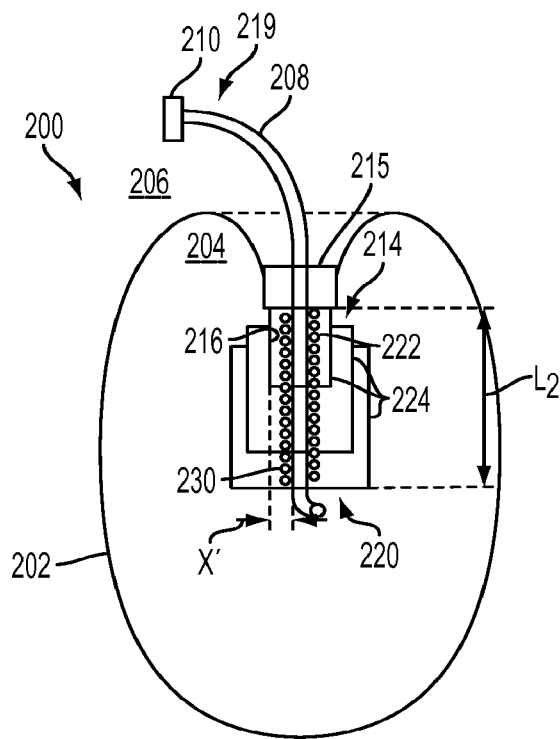
FIG. 3B shows the intragastric balloon of FIG. 3A with the telescoping internal tube in a shortened position, with the spring at the compressed length and the inflation tube disposed with a substantial portion outside the balloon in accordance with an embodiment of the invention.

FIGS. 3A and 3B show an intragastric balloon assembly 200 according to another embodiment of the invention. In this embodiment, structures similar to the preceding embodiments are similarly numbered and may not be discussed in full detail below. The internal tube 214 of FIGS. 3A and 3B is a telescoping tube having more than one telescoping segments 224 slideably engaged with each other. FIG. 3A shows the internal tube 214 in an extended position, whereas FIG. 3B shows the internal tube 214 in a contracted position.

The corresponding diameters D1, D2, D3 of the various telescoping segments 224 allow for one segment to slide within or over another. The diameter D1 of the smallest segment 224 must be sufficiently wide to accommodate the inflation tube 208. For example, there may be a space x' between the inflation tube 208 and the internal wall 216 of the telescoping segment 224 with diameter D1. The space x' may facilitate stretching and movement and/or sliding of the inflation tube 208 relative to the internal wall 216 of telescoping segment 224.

Figure 4A:
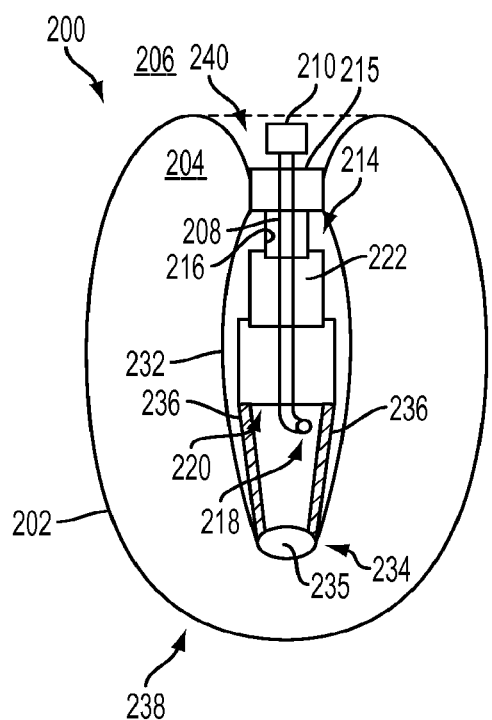
FIG. 4A shows an intragastric balloon with a telescoping internal tube in an extended position within a rigid support and a tether at a resting length, and an inflation tube disposed substantially inside the balloon in accordance with an embodiment of the invention.
Figure 4B:
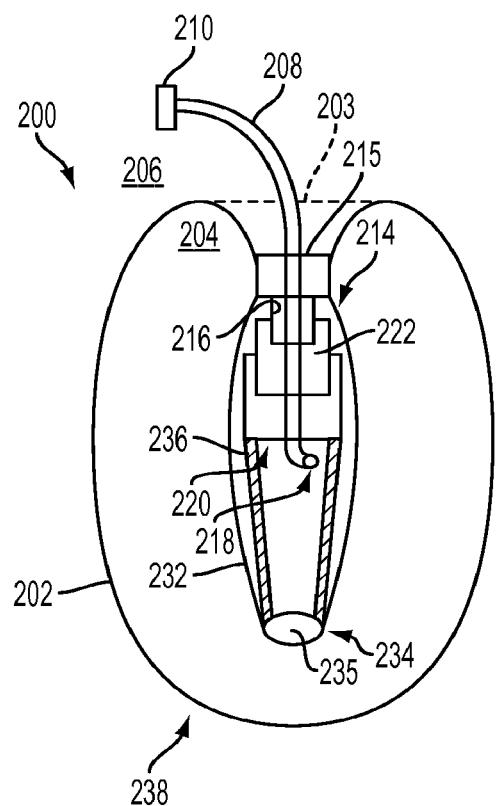
FIG. 4B shows the intragastric balloon of FIG. 4A with the telescoping internal tube in a shortened position within the rigid support and tether at a stretched length, and the inflation tube disposed with a substantial portion outside the balloon in accordance with an embodiment of the invention.

FIGS. 4A and 4B show an embodiment of the intragastric balloon assembly 200 that includes a rigid support structure 232 with one or more stretchable tethers or springs 236. Although only three telescoping segments 224 are shown in FIGS. 3A, 3B, 4A, and 4B, more or fewer may be used.

FIGS. 5-9 show additional embodiments of an intragastric balloon assembly 300 according to the invention. In FIGS. 5-9, a proximal end 319 of the inflation tube 308 includes one or more structures, including a valve 310 and a removable cap 312. The valve 310 can be selectively opened to perform an adjustment of the inflation level of the balloon 302, and closed when the adjustment is completed. The cap 310 can cover the valve 310 to seal it or to keep foreign particles or bacteria away from the valve.

Figure 5:
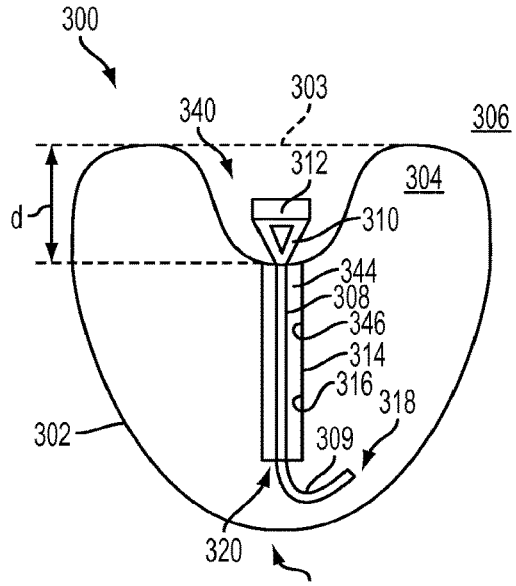
FIG. 5 shows an intragastric balloon with an internal tube and a recess to accommodate components of the intragastric balloon assembly in accordance with an embodiment of the invention.

To minimize the extent to which these external structures project outward from the balloon 302, a recess 340 is formed on the outer surface of the balloon 302. The recess 340 may have a depth d, as shown in FIG. 5, that is sufficient to house substantially all or some portion of the external structures, including valve 310 and cap 312, of the inflation tube 308 when the inflation tube 308 is in a resting (or non-stretched) position. In other words, a depth of the recess 340 may be greater than or equal to a height of the inflation tube 308 that is within the recess 340 in the resting position.

By allowing more of the inflation tube 308 and other related elements to be stored within the balloon 302 or recess 340, a smoother overall appearance of the balloon may be achieved by reducing or eliminating extension of those elements past a profile of the balloon, which is shown in FIG. 5 by a representative broken line 303. However, it may not be necessary for the inflation tube 308 and related elements to be completely within the balloon 302 or recess 340 in some embodiments. For example, a portion of the inflation tube 308, valve 310, or cap 312 may extend beyond the profile of the balloon.

Figure 6:
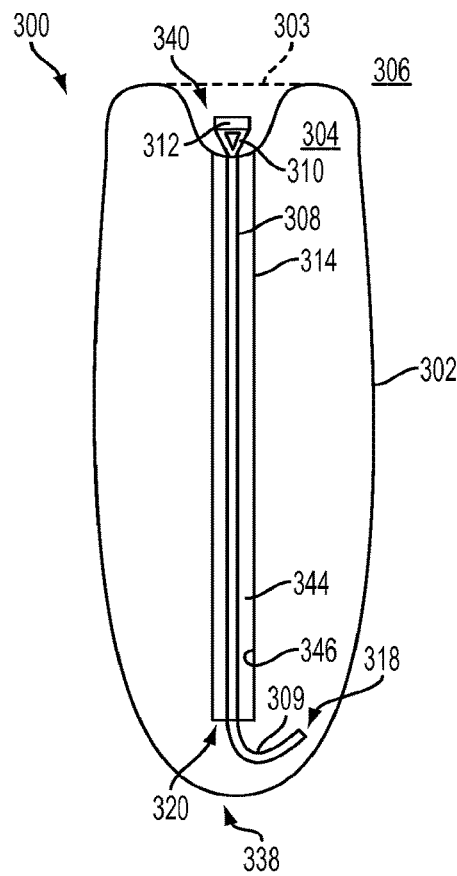
FIG. 6 shows an intragastric balloon with an elongated internal tube and a recess to accommodate components of the intragastric balloon assembly in accordance with an embodiment of the invention.

FIGS. 5 and 6 shows internal tubes 314 of different lengths. By providing an internal tube 314 of a certain length, a certain amount of inflation tube 308 may be stored within the internal tube 314. Thus, in some embodiments the internal tube 314 may be longer than other embodiments (e.g., compare FIG. 6 to FIG. 5) so that a longer inflation tube 308 may be used. A longer inflation tube 308 may also allow the inflation tube 308 to be stretch farther from the balloon 302.

Figure 7:
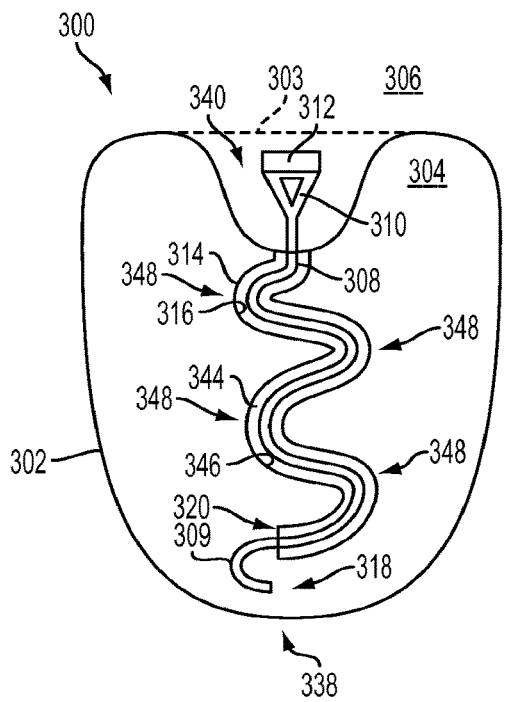
FIG. 7 shows an intragastric balloon with a curved internal tube and a recess to accommodate components of the intragastric balloon assembly in accordance with an embodiment of the invention.

FIG. 7 shows another embodiment where the internal tube 314 has a curved shape. The internal tube 314 includes a number of curved portions 348, corresponding to approximately two periods of a sinusoidal wave. Thus, curves 348 can accommodate an inflation tube 308 having a long effective length in a shorter balloon 302. The shape and curvature of the internal tube 314 can vary. For example, the curvature might be adjusted according to the friction between the internal tube 314 and the inflation tube 308 so that the inflation tube 308 can easily slide past the interior wall 316 of the internal tube 308 when being stretched or returning to the resting position.

To facilitate sliding of the inflation tube 308 within the internal tube 314, the interior wall 316 of the internal tube 314 may be formed of or coated with a low-friction or frictionless material or lubricant, or the internal tube 314 can be filled with a substance to reduce friction.

The inflation tube 308 of FIGS. 5-7 also includes a curved end portion 309 which can help prevent fluid flow from being blocked during inflation or deflation of the balloon. For example, it is possible that during deflation of some intragastric balloons an internal structure or tissue of the patient may be suctioned against the opening on the distal end of the inflation tube, which could block further deflation. The curved end portion 309 may prevent such a blockage. The curved end portion 309 may also be provided as an atraumatic end on the distal end 318 of the inflation tube 308. Thus, the curved end portion 309 may minimize the potential of the relatively sharp edges of the opening on the distal end 318 of the inflation tube 308 from contacting and possibly damaging an internal structure such as the balloon or the tissue of the patient.

Figure 8:
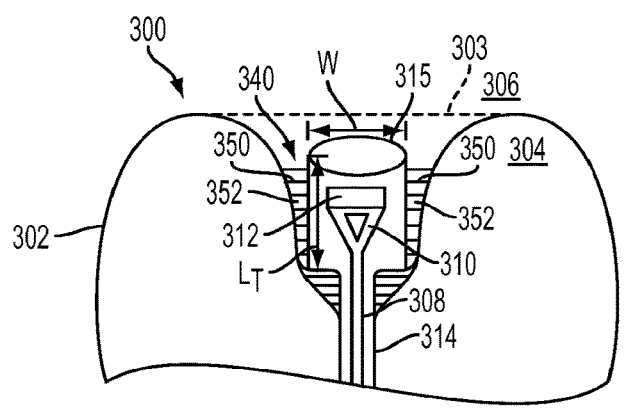
FIG. 8 shows a close-up view of a portion of an intragastric balloon with a recess in accordance with an embodiment of the invention.

In FIG. 8, a receptacle 315 is provided within the recess 340. The receptacle 315 is sized to accommodate the external structures, such as the cap 312 and valve 310. A filler substance 350 may be used to fill a space 352 between the receptacle 315 and the walls of the recess 340. Such a filler substance 350 can be used to bond the receptacle 315 to the balloon 302 and to keep external matter or bacteria from becoming trapped in the space 352. In an embodiment, the filler substance 350 may be some type of glue or epoxy. In addition, the receptacle 315 may serve to form or hold the shape of the recess 340.

In some embodiments, walls of the balloon 302 surrounding the opening or receptacle 315 may involute and be attached or glued to the receptacle 315 and/or internal tube 314, as shown in FIG. 8, for example. The receptacle 315 may either be formed from the proximal end of the internal tube 314 or be a structure that is attached to the proximal end of the internal tube 314 via glue, adhesive, or some structure attachment mechanism. The receptacle 315 that is outside of the balloon 302, though it may still be within the balloon profile shown in FIG. 8 by a representative broken line 303, may be made formed as a soft flexible catheter. However, in an embodiment, the receptacle 315 nonetheless has sufficient firmness to help maintain the shape of the recess 340, even as the volume of the balloon is adjusted or the shape of the balloon changes. Furthermore, the material and stiffness of the receptacle 315 can prevent the components disposed within the receptacle 315 from making harmful or injurious contact with internal tissues of the patient. Additionally, the receptacle 315 is itself of suitable construction to not injure the tissue of the patient while maintaining the shape of the balloon under normal operating conditions and pressures. The receptacle 315 may therefore provide protection for the inflation tube 308, valve 310, and cap 312 that are disposed within it, while also not being injurious to internal organs or tissue of a patient.

Figure 9:
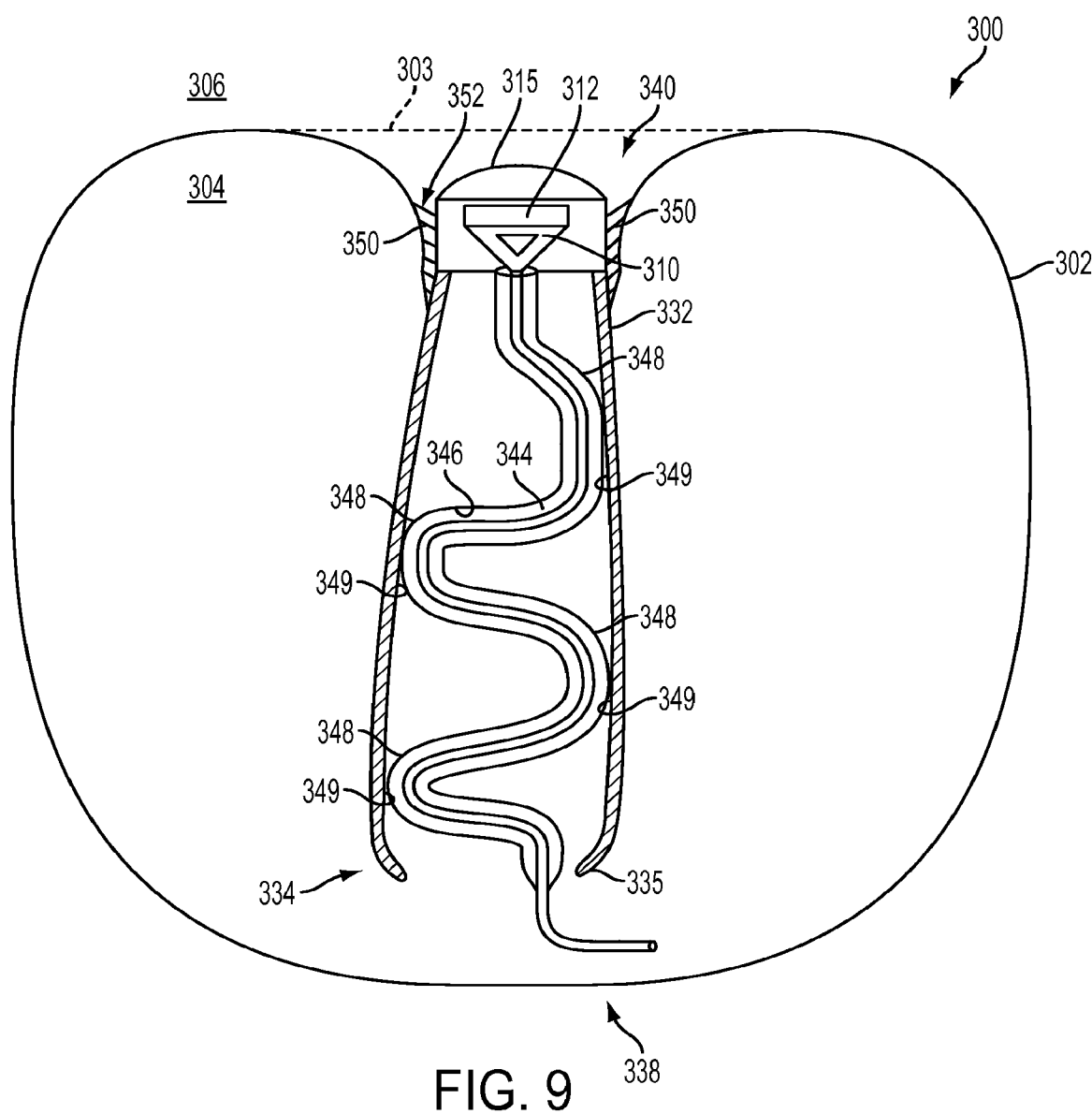
FIG. 9 shows an intragastric balloon with a support and internal curved tube in accordance with an embodiment of the invention.

FIG. 9 shows an embodiment with a rigid support structure 332. The internal tube 314 in FIG. 9 has a curved shape with the curved sections 348 being attached to the rigid support structure 332 at anchor points 349. The internal tube 314 of this embodiment may have a frictionless or low-friction internal canal 344. For example, the internal canal 344 may have a lining 346 to facilitate movement of the inflation tube 308 relative to the internal tube 314.

In the above embodiments, the rigid support structure 132, 232, 332 may be formed, for example, as a tubular or cylindrical structure, or may be formed as one or more beams in a support frame.

Embodiments of the invention may provide a system and method for internalizing external components of an intragastric balloon within the balloon. However, some embodiments provide for a portion of these external components to remain on an outside of the balloon. In some embodiments, an internal tube houses a stretchable inflation tube. The stretchable tube may be bonded at its distal end to an inner surface of the internal tube, thereby allowing the remainder of the inflation tube to slide freely within the lumen of the internal tube and thereby attain its maximum stretched length outside of the balloon. For example, the stretchable inflation tube may be bonded in its most distal 1 cm to the internal surface of the rigid catheter. In such an example, a 10 cm long inflation tube can stretch the 9 cm that are unbound to lengths of 60-90 cm.

The internal tube may be a fixed length and therefore hold only a set length of the stretchable inflation tube. However, in embodiments of the invention, the internal tube can be made to have a changeable length such that at a resting state it is one length, but when pulled it can shorten. In a shortened state of the internal tube, the stretchable inflation tube may then extend farther from the balloon. In addition, the length of the inflation tube can be decreased due to the increase distance provided by the shortened internal tube.

In some embodiments, for example, when the inflation tube is pulled or stretched away from the balloon to facilitate inflation or adjustment of the volume of the balloon, the internal tube is shortened or compressed as it is pulled by the distal end of the inflation tube. When the inflation tube is released from its pulled or stretched position, the internal tube will return from the shortened or compressed state to a resting or un-compressed state. In returning to the resting or un-compressed state, the internal tube pulls the distal end of the inflation tube to assist in returning the inflation tube its resting state such that the inflation tube is in the interior of the balloon, substantially within the interior of the balloon, or within the general profile of the balloon.

According to some embodiments, the internal tube may have segments of accordion walls that contract when pulled to shorten the length of the internal tube. The structure of the accordion walls can be varied such that they will have more or less propensity to return to the baseline longer length. For example, a thickness of the accordion walls can be varied. In addition, or alternatively, a spring can be provided that promotes lengthening of the internal tube. Such a spring can be made of metal and can be disposed an internal or an external side of the internal tube.

In some embodiments, the distal end of the variable sized internal tube can be coupled to a distal end of a surrounding structure, such as a rigid support structure. These may be coupled by, for example, a stretchable tether or spring that promotes lengthening of the internal tube to its longer length. Alternatively, the internal tube can be coupled to a distal balloon wall by a stretchable tether or spring that promotes lengthening of the internal tube to its longer length According to some embodiments, the internal tube can be formed of telescoping segments (e.g., an old-fashioned television antenna-like structure) that houses progressively smaller diameter tubes that can shorten or lengthen as desired similar to the accordion structures of an above-discussed embodiment. The inflation tube may fit within the smallest diameter segment of the telescoping internal tube. The smallest segment can therefore have a diameter large enough to accommodate the inflation tube. In some embodiments, a space between the inflation tube and the internal tube is provided. For example, the space may be at least 1 mm.

In some embodiments, any external catheter, including the inflation tube, as well as the valve and cap on the inflation tube may be internalized within the balloon or within an outer shape of the balloon. As a result, a smooth balloon without any external protrusions may be provided. This can be accomplished in several ways. In some embodiments, the area of the balloon from which the catheter or external components exit will be shaped to form a recess or concavity. The recess may be deep enough to hold the external portion of the catheter, including the valve and cap. For example, the recess may be approximately 1-5 cm deep. The recess may be created by differing the density of the balloon wall or silicone, or by adding other materials to the wall of the balloon in the area of the recess. For example, the balloon may comprise a silicone wall having varying thickness, or multiple silicone materials of different stiffnesses. Additionally, materials, such as internal layers of materials, may be added to the balloon. Such layers may be formed in mesh or solid structures. In an embodiment, multiple layers of silicon may be used with intervening mesh layers. Other materials may also be used, including, for example, polypropylene, polyethylene, nylon, and latex.

In some embodiments, the valve may comprise a silicone housing with a luer lock neck that can be closed with the cap. The housing may have a funnel or tapered shape. The funnel may contain a one-way or two-way valve that is made from hard material such as polypropylene, or it may contain a valve made of a soft material such as silicone. The funnel could then be closed with a soft material such as silicone in the shape of a thin rubber sheath that rolls on and off. The thin rubber sheath may have a cylindrical shape with a closed first end and an open second end. The soft material version would be utilized to prevent tissue damage.

In some embodiments, the balloon can be elongated such that an internal tube or catheter can be longer and house more of the inflation tube, leaving less to protrude outside of the balloon. According to various embodiments, the balloon can be spherical, pear-shaped, cylindrical, or other shapes that fit in the stomach.

In some embodiments, the inflation tube may stretch 6-10 times its length. In other embodiments, the inflation tube may stretch 10-20 times its length. The inflation tube may be made from different silicone material having different stretchability or elasticity.

In some embodiments, the internal tube or catheter may be formed as a solid, straight catheter and may be made from, for example, silicone. In some embodiments, the internal tube or catheter that houses the inflation tube can be modified to house a frictionless internal canal that houses the inflation tube. For example, the internal tube can be lined with TEFLON® or other similar materials, or filled with liquid silicone oil or other friction reducing material. The reduced fiction can help enable internal tubes of different shapes and paths according to some embodiments. For example, the internal tube may curve in a sinusoidal pattern. In this way, the effective length of the internal tube is increased over a limited straight-line distance. Therefore, the internal tube may be allowed to contain more of the inflation tube inside the balloon.

The internal tube may be provided as one piece that starts internally and is glued to the top of the balloon, after which it exits the balloon. According to some embodiments, the internal tube can be changed to a completely internal tube or catheter that ends in a receptacle at its glue point with the balloon. The receptacle is big enough to house the valve and cap of the inflation tube.

Any combination of all of the above can accomplish the internalization of the external catheter, valve and cap, with a supporting frame that can also act as an anchor.

Some embodiments of the present invention relate to the elimination of the guide wire and pusher used during the insertion process of an intragastric balloon. For example, the insertion procedure may include the balloon being attached to an endoscope and pulled into the stomach during a routine endoscopy procedure. The balloon may then be released from the endoscope and inflated. This process can be accomplished in several ways.

In some embodiments, the balloon may be folded in a way to allow it to be wrapped around the endoscope. Additionally, a cylindrical containing member or wrapping piece may be attached to the distal end of the endoscope. Such a wrapping piece can be made to fit snugly on one or all endoscope sizes, and/or may be adjustable to different size endoscopes. The wrapping piece may be made of a pliable material including, for example, silicone, rubber, polymer or other pliable material, or of a non-pliable material such as a fabric that can hold the balloon. The wrapping material may be able to securely hold, for example, about 2-15 cm of the balloon length during the insertion of the endoscope into the stomach.

Once in the stomach, the balloon is separated from the endoscope. This can be accomplished in several ways. In some embodiments, the wrapping piece can have perforations on its surface such that inflation of the balloon will expand the wrapping piece and the perforations will open and release the balloon. Alternatively, the inflation of the balloon may automatically push the balloon out of the wrapping piece's grasp. Alternatively, the proximal edge of the wrapping piece may be connected to a string that enters a biopsy channel at the distal end of the endoscope. The string, which may exit the top of the biopsy channel, may be pulled to pull the proximal edge of the wrapping piece distally and thereby release the balloon.

Some embodiments of the invention relate to a method of adjusting an inflation level of a balloon inserted into a stomach of a subject where the balloon is in fluid communication with an inflation tube. The method includes stretching the inflation tube while keeping the balloon in the stomach. The inflation tube will extend from within the balloon when stretching. In its extended position, a fluid is transferred to or from the balloon via the inflation tube to adjust the inflation level of the balloon. Subsequently, the inflation tube is returned to a resting position after adjusting the inflation level. In this resting position, a substantial portion of the inflation tube is contained within the balloon or within a recess on the outer surface of the balloon. Thus, the balloon has reduced protrusions on the exterior.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

In some embodiments, the internal tube may be made of a shape-memory material to facilitate a return of the internal tube to the resting position.

FIGS. 10A-10D and 11A-C show an intragastric balloon and endoscope assembly 400 according to additional embodiments of the invention.

An adjustable balloon may be a fluid filled balloon that has a stretchable inflation tube connected to the balloon. The inflation tube exits the balloon within a surrounding tube and ends in a valve. During an insertion procedure, a pusher and a firm guidewire within the pusher may connect to the balloon and an external catheter in one straight continuum. The inflation tube may stretch about 6 to 10 times its length, and may allow the valve to be pulled out of the stomach while the balloon remains in the stomach. This can allow adjustment of the volume of the balloon. Applicant's other patent applications referenced and incorporated above discuss some features of a similar balloon.

In some embodiments, systems and methods are provided to eliminate the guidewire and pusher sometimes used during the insertion process. In an embodiment, the balloon may be attached to an endoscope and pulled into the stomach during a routine endoscopy procedure. The balloon may then be released from the endoscope and inflated. This release and inflation can be accomplished in several ways. For example, in an embodiment, the balloon is folded in a way to allow it to be wrapped around the endoscope. In addition, a cylindrical wrapping piece may be provided and attached to a distal end of the endoscope. The wrapping piece may fit snugly on different sized endoscopes and/or may be adjustable to different size endoscopes. The wrapping piece can be made of a pliable material such as silicone or rubber, or a non-pliable material such as a fabric. The wrapping piece may be configured to hold the balloon (for example, about 2-15 cm of the length of the balloon) securely during the insertion of the endoscope into the stomach. Once in the stomach, the balloon may be separated from the endoscope. In an embodiment, the wrapping piece can have perforations on its surface such that inflation of the balloon will expand the wrapping piece and the perforations will open and release the balloon. Alternatively, the inflation of the balloon will automatically push the balloon out of the grasp of the wrapping piece. Alternatively, the proximal edge of the wrapping piece may be connected to a string that enters a biopsy channel at the distal end of the endoscope. The string exits the top of the biopsy channel, and, when pulled, can pull the proximal edge of the wrapping piece distally to release the balloon.

Figure 10A:
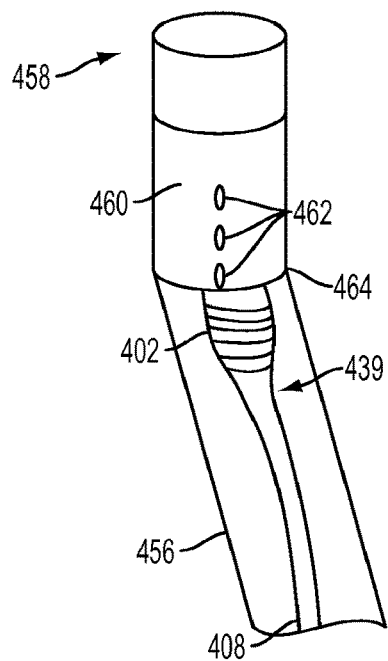
FIG. 10A shows an intragastric balloon and endoscope assembly before expansion of the balloon and with a containing member having perforations in accordance with an embodiment of the invention.
Figure 10B:
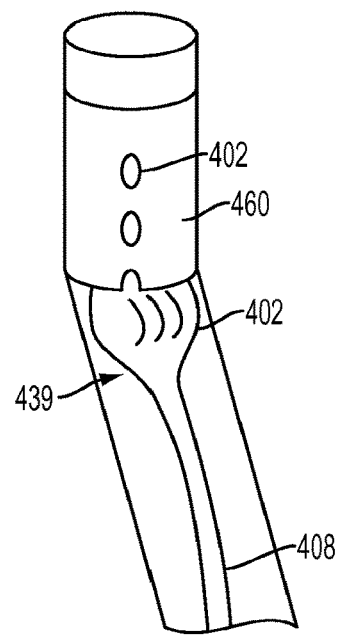
FIG. 10B shows the intragastric balloon and endoscope assembly of FIG. 10A during expansion of the balloon and shows widening of the perforations from a partially expanded state of the balloon in accordance with an embodiment of the invention.
Figure 10C:
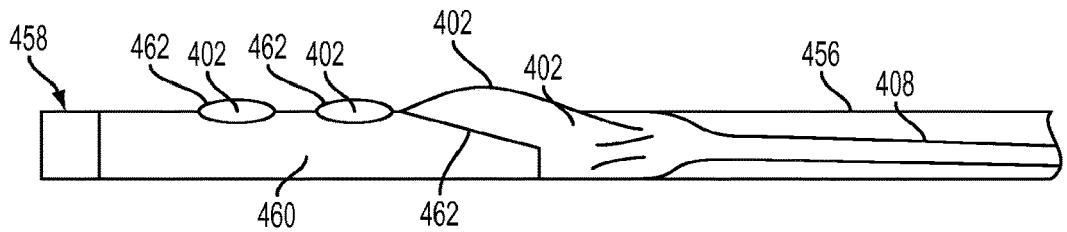
FIG. 10C shows the intragastric balloon and endoscope assembly of FIG. 10A from a side view during expansion of the balloon and shows expansion of the balloon through the perforations in accordance with an embodiment of the invention.
Figure 10D:
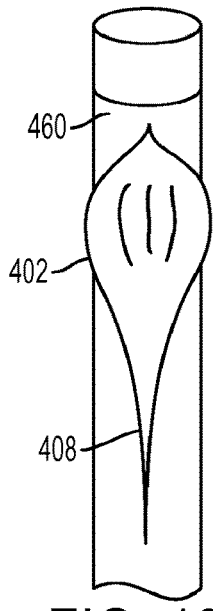
FIG. 10D shows the intragastric balloon and endoscope assembly of FIG. 10A during further expansion of the balloon after tearing of the perforations in accordance with an embodiment of the invention.

In FIG. 10A, the balloon 402 is attached to or wrapped around the distal end 458 of an endoscope 456 and covered or held in place by a wrapping 460. The wrapping 460 may include perforations 462. As shown in FIGS. 10B and 10C, the perforations can expand and/or allow the wrapping 460 to tear when the balloon 402 is inflated. The perforations may be placed toward a proximal edge 464 of the wrapping 460 to control the tear and to release the balloon on the proximal side, as shown in FIG. 10D.

Figure 11A:
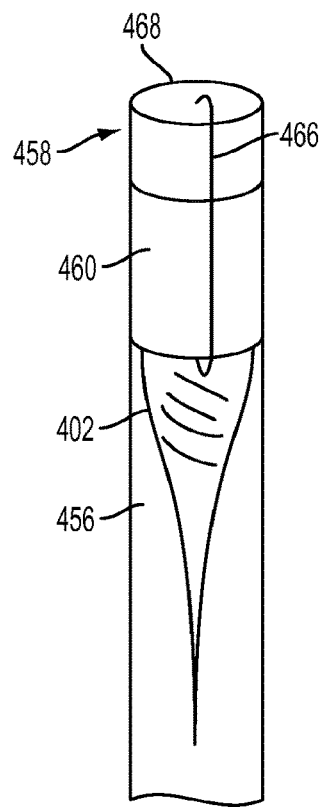
FIG. 11A shows an intragastric balloon and endoscope assembly with a containing member in a state for insertion of the assembly in a patient's body in accordance with an embodiment of the invention.
Figure 11B:
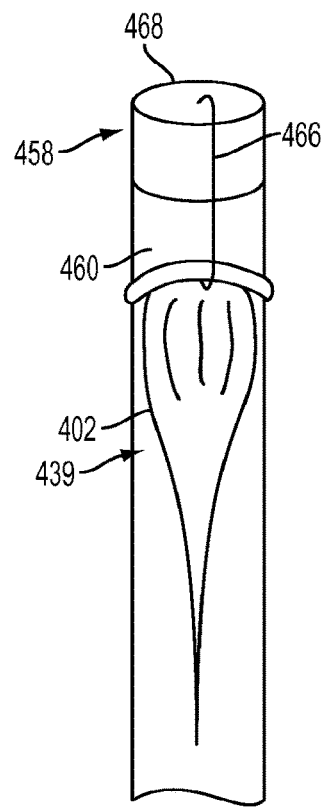
FIG. 11B shows the intragastric balloon and endoscope assembly of FIG. 11A during removal of the containing member in accordance with an embodiment of the invention.
Figure 11C:
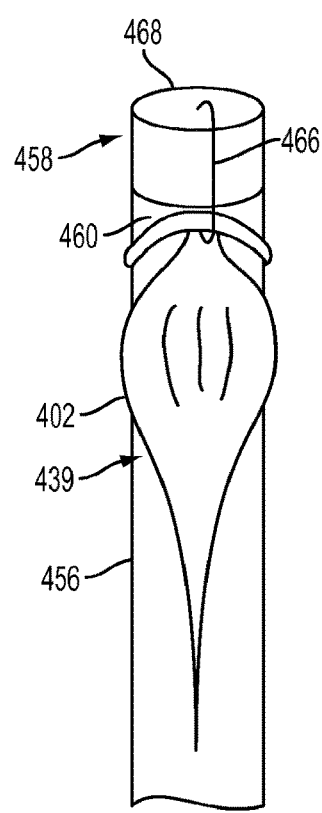
FIG. 11C shows the intragastric balloon and endoscope assembly of FIG. 11A after the containing member has been substantially removed from the balloon in accordance with an embodiment of the invention.

In FIG. 11A, the wrapping 460 is coupled to a string 466. The wrapping 460 is removed by the string 466 being pulled from the biopsy channel 468 to remove the wrapping 460 by pulling the proximal edge 464 of the wrapping 460, as shown in FIGS. 11B and 11C.

The invention claimed is:

1. An apparatus for use in a stomach of a subject, the apparatus comprising:
   a balloon adapted for placement in the stomach and having an opening to an interior of the balloon;
   an internal tube in the interior of the balloon with a proximal end coupled to the opening of the balloon; and
   an inflation tube having a distal end in the interior of the balloon and a proximal end configured to receive a fluid on an exterior of the balloon, the inflation tube being configured to stretch from the stomach to a mouth of the subject to facilitate inflation of the balloon and to have a resting position that is within the general profile of the balloon, the internal tube being disposed around at least a portion of the inflation tube that is in the interior of the balloon,
   wherein the internal tube has a variable length including a first length that accommodates a substantial portion of the inflation tube when the inflation tube is in the resting position, and a second length, which is shorter than the first length, when the inflation tube is stretched outwardly from the balloon.

2. The apparatus according to claim 1, wherein a distal end of the internal tube is coupled to the distal end of the inflation tube.

3. The apparatus according to claim 1, wherein a wall of the internal tube has one or more accordion structures to facilitate the variable length of the internal tube.

4. The apparatus according to claim 1, further comprising:
   a spring coupled to the internal tube, the spring biasing the internal tube to a first position.

5. The apparatus according to claim 1, wherein the internal tube comprises a plurality of telescoping segments slideably engaged with each other.

6. The apparatus according to claim 1, further comprising:
   a rigid support in the interior of the balloon disposed around, and extending coaxially with, the internal tube.

7. The apparatus according to claim 6, wherein a distal end of the internal tube is coupled to a distal end of the rigid support via a stretchable tether such that the stretchable tether is stretched when the internal tube is in a second position thereby biasing the internal tube toward a first position.

8. The apparatus according to claim 1, wherein the inflation tube comprises:
   a valve on the proximal end of the inflation tube configured to selectively open and close the inflation tube, and
   a removable cap on the proximal end of the inflation tube covering the valve.

9. The apparatus according to claim 1, wherein the opening of the balloon is disposed within a recess formed in an exterior surface of the balloon.

10. The apparatus according to claim 9, wherein the proximal end of the inflation tube is disposed within the recess in the resting position of the inflation tube.

11. The apparatus according to claim 10, wherein a depth of the recess is greater than or equal to a height of the inflation tube that is within the recess in the resting position.

12. The apparatus according to claim 9, the apparatus further comprising:
   a receptacle disposed within the recess and configured to surround the proximal end of the inflation tube when in the resting position.

13. The apparatus according to claim 12, wherein a gap between a wall of the recess and an outer wall of the receptacle is filled with a filler substance.

14. The apparatus according to claim 1, wherein the internal tube has a curved shape to increase a length of the inflation tube contained within the internal tube.

15. The apparatus according to claim 1, wherein a lumen wall of the internal tube is configured to allow sliding of the inflation tube relative to the lumen wall.

16. An apparatus for use in a stomach of a subject, the apparatus comprising:
   a balloon adapted for placement in the stomach and having an opening to an interior of the balloon;
   an internal tube in the interior of the balloon with a proximal end coupled to the opening of the balloon;
   an inflation tube having a distal end in the interior of the balloon and a proximal end configured to receive a fluid on an exterior of the balloon, the inflation tube being configured to stretch from the stomach to a mouth of the subject to facilitate inflation of the balloon and to have a resting position that is within the general profile of the balloon, the internal tube being disposed around at least a portion of the inflation tube that is in the interior of the balloon; and
   a receptacle disposed within a recess and configured to surround the proximal end of the inflation tube when in the resting position.

17. The apparatus according to claim 16, wherein the internal tube has a variable length including a first length that accommodates a substantial portion of the inflation tube when the inflation tube is in the resting position, and a second length, which is shorter than the first length, when the inflation tube is stretched outwardly from the balloon.

18. The apparatus according to claim 16, wherein the internal tube has a curved shape to increase a length of the inflation tube contained within the internal tube.

19. A method of adjusting an inflation level of a balloon inserted into a stomach of a subject where the balloon is in fluid communication with an inflation tube, the method comprising:
   providing the apparatus according to claims 1 or 16;
   stretching the inflation tube while keeping the balloon in the stomach, the inflation tube extending from within the balloon when stretching;

transferring a fluid to or from the balloon via the inflation tube which may or may not require connection to an extension tube, to adjust the inflation level of the balloon; and returning the inflation tube to a resting position after adjusting the inflation level, a substantial portion of the inflation tube being contained within the balloon in the resting position.

20. The method according to claim 19, further comprising:

positioning a proximal end of the inflation tube within a recess formed on an exterior of the balloon when returning the inflation tube to the resting position.

\* \* \* \* \*